US010485890B1

(12) United States Patent
Sabankaya (10) Patent No.: US 10,485,890 B1
(45) Date of Patent: Nov. 26, 2019

(54) METHOD FOR SELECTIVELY INDUCING VARIOUS EMOTIONAL STATES IN A VEHICLE WITH MULTIPLE AROMATHERAPY COMPOSITIONS

(71) Applicant: Chera Sabankaya, Weed, CA (US)

(72) Inventor: Chera Sabankaya, Weed, CA (US)

( * ) Notice: Subject to any disclaimer, the term of this patent is extended or adjusted under 35 U.S.C. 154(b) by 0 days.

(21) Appl. No.: 15/791,239

(22) Filed: Oct. 23, 2017

Related U.S. Application Data (60) Provisional application No. 62/417,190, filed on Nov. 3, 2016.

(51) Int. Cl.
| | |
|---|---|
| *A61K 36/53* | (2006.01) |
| *A61L 9/013* | (2006.01) |
| *A61L 9/04* | (2006.01) |
| *A61L 9/14* | (2006.01) |
| *A61K 8/04* | (2006.01) |
| *B60H 3/00* | (2006.01) |
| *A61Q 13/00* | (2006.01) |
| *A61K 8/92* | (2006.01) |

(52) U.S. Cl.
CPC .............. *A61L 9/013* (2013.01); *A61K 8/042* (2013.01); *A61K 8/922* (2013.01); *A61L 9/04* (2013.01); *A61L 9/14* (2013.01); *A61Q 13/00* (2013.01); *B60H 3/0028* (2013.01); *B60H 3/0035* (2013.01); *A61L 2209/13* (2013.01)

(58) Field of Classification Search
None
See application file for complete search history.

(56) References Cited

U.S. PATENT DOCUMENTS

| | | | |
|---|---|---|---|
| 1,556,714 A | 10/1925 | Ridgely | |
| 4,806,274 A | 2/1989 | Crouse et al. | |
| 5,078,792 A | 7/1992 | Hinkle et al. | |
| 5,429,180 A * | 7/1995 | Nishino | A61L 9/12 165/41 |
| 6,361,615 B1 * | 3/2002 | Callahan | C11D 1/72 134/34 |
| 6,838,492 B2 | 7/2005 | Maleeny et al. | |
| 7,824,715 B2 * | 11/2010 | Behan | A61L 9/00 424/443 |
| 10,150,351 B2 * | 12/2018 | Lin | G06K 9/00845 |
| 10,232,075 B2 * | 3/2019 | Banco | A61L 9/125 |
| 2015/0064060 A1 * | 3/2015 | McCaughey | A61L 9/01 422/4 |
| 2016/0195856 A1 * | 7/2016 | Spero | G06N 5/046 700/90 |
| 2016/0361972 A1 * | 12/2016 | Blackley | B60H 3/0035 |

FOREIGN PATENT DOCUMENTS

| | | | |
|---|---|---|---|
| CN | 104888262 | * | 9/2015 |
| KR | 1837912 | * | 3/2018 |
| WO | WO 2007/105506 | * | 9/2007 |

OTHER PUBLICATIONS

Dmitrenko, D. et al. A Comparison of Scent Delivery Devices and Their Meaningful Use for In-Car Olfactory Interation. Proceedings of the 8th International Conference on Automotive User Interfaces and Interactive Vehicular Applications pp. 23-26, Oct. 24-26, 2016. (Year: 2016).*
Around III-VS. 18(2)56, Mar. 2005. (Year: 2005).*

* cited by examiner

*Primary Examiner* — Ralph J Gitomer
(74) *Attorney, Agent, or Firm* — Jerry Haynes Law (57) ABSTRACT

A kit and a method for selectively inducing various emotional states of an occupant in a vehicle with multiple aromatherapy compositions that strategically infuses eclectic aromatherapy compositions into an interior passenger compartment of a vehicle. The aromatherapy compositions are formulated to achieve various emotional states. A vehicle occupant selects an appropriate aromatherapy composition based on the desired emotional state. The occupant may change compositions at regular durations when a new emotional state is desired. The composition is integrated into the ventilation system of the vehicle causing the composition to vaporize and be drawn into the vehicle passenger compartment for diffusion into the passenger compartment. The passenger may: 1) use the same aromatherapy composition throughout the duration in the passenger compartment to maintain the same emotional state; 2) change the aromatherapy composition at any time during the duration in the passenger compartment to change the emotional state; or 3) mix multiple aromatherapy compositions to create an occupant-defined emotional state.

9 Claims, 5 Drawing Sheets

| AROMATHERAPY RECIPES FOR ANXIETY ||||
| --- | --- | --- | --- |
| BLEND 1 | BLEND 2 | BLEND 3 | BLEND 4 |
| • 2 DROPS BERGAMOT<br><br>• 2 DROPS CLARY SAGE<br><br>• 1 DROP FRANKINCENSE | • 3 DROPS SANDALWOOD<br><br>• 2 DROPS BERGAMOT | • 3 DROPS LAVENDER<br><br>• 2 DROPS CLARY SAGE | • 1 DROP ROSE<br><br>• 1 DROP LAVENDER<br><br>• 2 DROPS MANDARIN<br><br>• 1 DROP VETIVER |

FIG. 5

| AROMATHERAPY RECIPES THAT MAY HELP ENHANCE ENERGY AND ALERTNESS ||||
| --- | --- | --- | --- |
| BLEND 1 | BLEND 2 | BLEND 3 | BLEND 4 |
| • 2 DROPS BASIL<br><br>• 1 DROP CYPRESS<br><br>• 2 DROPS GRAPEFRUIT | • 3 DROPS GRAPEFRUIT<br><br>• 2 DROPS GINGER | • 2 DROPS ROSEMARY<br><br>• 3 DROPS BERGAMOT | • 2 DROPS PEPPERMINT<br><br>• 1 DROP FRANKINCENSE<br><br>• 2 DROPS LEMON |

FIG. 6

| AROMATHERAPY RECIPES FOR HAPPINESS | | | |
|---|---|---|---|
| BLEND 1 | BLEND 2 | BLEND 3 | BLEND 4 |
| • 3 DROPS BERGAMOT<br><br>• 1 DROP YLANG YALANG<br><br>• 1 DROP GRAPEFRUIT | • 1 DROP GERANIUM<br><br>• 2 DROPS FRANKINCENSE<br><br>• 2 DROPS ORANGE | • 2 DROPS SANDALWOOD<br><br>• 1 DROP ROSE<br><br>• 2 DROPS BERGAMOT | • 2 DROPS LEMON, ORANGE OR BERGAMOT<br><br>• 2 DROPS GRAPEFRUIT<br><br>• 1 DROP YLANG YLANG, ROSE OR NEROLI |

FIG. 7

| AROMATHERAPY RECIPES FOR ANGER | | | |
|---|---|---|---|
| BLEND 1 | BLEND 2 | BLEND 3 | BLEND 4 |
| • 1 DROP ROSE<br><br>• 3 DROPS ORANGE<br><br>• 1 DROP VETIVER | • 3 DROPS BERGAMOT<br><br>• 1 DROP YLANG YLANG<br><br>• 1 DROP JASMINE | • 1 DROP ROMAN CHAMOMILE<br><br>• 2 DROPS BERGAMOT<br><br>• 2 DROPS ORANGE | • 3 DROPS ORANGE<br><br>• 2 DROPS PATCHOULI |

METHOD FOR SELECTIVELY INDUCING VARIOUS EMOTIONAL STATES IN A VEHICLE WITH MULTIPLE AROMATHERAPY COMPOSITIONS

CROSS-REFERENCE TO RELATED APPLICATIONS

This application claims priority from U.S. Provisional Application Ser. No. 62/417,190, entitled "Method for Selectively Inducing Various Emotional States in a Vehicle with Multiple Aromatherapy Compositions", filed Nov. 3, 2016, which application is hereby incorporated herein by reference in its entirety.

FIELD OF THE INVENTION

The present invention relates generally to a kit and a method for selectively inducing various emotional states in a closed compartment with multiple aromatherapy compositions. More so, the present invention relates to a kit and a method which infuse eclectic aromatherapy compositions into an interior passenger compartment of a vehicle through selective integration of at least one aromatherapy composition into the ventilation system of the vehicle.

BACKGROUND OF THE INVENTION

Many people place air fresheners in a room or in a vehicle to cover up odors in the room or vehicle or just to add a fragrant scent to the air. Many air fresheners are commercially available, though often they are mere imitations; while synthetics may smell like the real thing. Sometimes some aromatherapy compositions are used in a room, though most of these provide for only one scent at a time.

Essential oils have been used for thousands of years in aromatherapy. One of the oldest methods is distillation practiced in ancient Persia, Turkey, and India thousands of years ago. Aromatic substances were also used by the ancient Chinese, Egyptians and Greeks as medicinal perfumes. In the 10th century the Arabs were extracting essential oils from aromatic plants and using them medicinally. The Knights of the Crusades brought aromatic essences and waters back to Europe from the Middle East and they became so popular that perfume began to be manufactured and was well established by the end of the 12th century. By the turn of the 18th century essential oils were widely used in medicinal preparations and Salmon's dispensary of 1896 contains recipes for numerous aromatic remedies.

Numerous innovations have been provided in prior art that are adapted to use as ascent or air fresheners or scented paint or coating or aromatic compositions. Even though these innovations may be suitable for the specific purposes to which they address, however, they would not be as suitable for the purposes of the present invention.

U.S. Pat. No. 4,806,274 to Crouse et al. describes a scented cleaner composition for outdoor sporting equipment such as guns, wherein the composition includes a primary cleaning component and a scent component from an aromatic live plant extract.

U.S. Pat. No. 5,078,792 to Hinkle et al. teaches a scented paint composition, wherein the composition is manufactured by mixing a predetermined masking agent with a selected paint pigment. A selected solvent is mixed with the pigment to form a paint solution. A predetermined inducing agent and a selected scent extract are mixed with the paint solution such that the inducing agent disperses the scent extract throughout the paint solution to provide the paint solution with a select scent.

U.S. Pat. No. 6,361,615 to Callahan discloses a cleaning compound additive for water or windshield wiper fluid to aid removal of insect splatters from a windshield. The cleaning compound additive includes dry particulate orange dye and dry particulate citrus orange scent along with other chemicals and insect repellants.

U.S. Pat. No. 6,838,492 to Maleeny et al. describes a paint scenting additive mixture formulated to be introduced into paint compositions as a stable dispersion therein to produce a scented paint that provides a pleasant and long-lasting fragrance or aroma in an ambient surrounding.

U.S. Pat. No. 20150064060 to McCaughey et al. teaches a method to provide air freshener, scent, fragrance or perfume to an automobile in a milder and evenly applied manner. The additive or premixed fluid is combined with windshield washer fluid where it may be dispensed or applied on the exterior of the windshield. It is pulled from the outside of the car and vented into the automobile, for use as an interior air freshener.

It is apparent now that numerous innovations that are adapted for use as a scent or air freshener or scented paint or coating or aromatic compositions have been developed in the prior art that are adequate for various purposes. Furthermore, even though these innovations may be suitable for the specific purposes to which they address, accordingly, they would not be suitable for the purposes of the present invention as heretofore described. Thus a kit and a method which infuse eclectic aromatherapy compositions into an interior passenger compartment of a vehicle through selective integration of at least one aromatherapy composition into the ventilation system of a closed compartment such as compartment of a vehicle is therefore needed.

SUMMARY OF THE INVENTION

The present invention describes a kit and method that infuse eclectic aromatherapy compositions into an interior passenger compartment of a vehicle through selective integration of at least one aromatherapy composition into the ventilation system of the vehicle; thereby enabling a passenger to select a desired aromatherapy composition, or mixed combinations thereof, to achieve a desired emotional state.

According to one aspect of the present invention, a method for selectively inducing various emotional states of an occupant in a vehicle with multiple aromatherapy compositions includes formulating multiple aromatherapy compositions, whereby each aromatherapy composition is configured to induce a unique emotional state; integrating at least one of the multiple aromatherapy compositions into a ventilation system of a vehicle; vaporizing the at least one of the multiple aromatherapy compositions; diffusing the at least one of the multiple aromatherapy compositions into a passenger compartment of the vehicle; inducing an emotional state in a passenger; selecting a subsequent aromatherapy composition; integrating the subsequent aromatherapy composition into the ventilation system of the vehicle to induce a subsequent emotional state in the passenger; mixing multiple aromatherapy compositions; and integrating the mixed aromatherapy compositions into the ventilation system of the vehicle to induce a user defined emotional state in the passenger.

According to another aspect of the present invention, a kit comprising multiple aromatherapy compositions for selectively inducing various emotional states in a closed compartment, wherein the kit comprising multiple aromatherapy compositions includes a lavender and potpourri aromatherapy composition; a sweet apple aromatherapy composition; a rose and potpourri aromatherapy composition; a relaxing aromatherapy composition; an anxiety relief aromatherapy composition; an energy inducing aromatherapy composition; a happiness inducing aromatherapy composition; and an anger reducing aromatherapy composition, wherein the kit allows integrating at least one of the multiple aromatherapy compositions into a ventilation system of the closed compartment, thereby allowing vaporization and diffusion of the at least one of the multiple aromatherapy compositions into the compartment.

In view of the foregoing, it is therefore an objective of the present invention to provide a method for selectively inducing various emotional states of an occupant in a vehicle compartment with multiple aromatherapy compositions.

Another objective is to provide a kit comprising multiple aromatherapy compositions for selectively inducing various emotional states in a closed compartment.

Another objective is to enable the user to change or mix the aromatherapy compositions, so as to induce a subsequent or user defined emotional state.

Another objective is to integrate the aromatherapy compositions into a ventilation system of the closed compartment.

Another objective is to utilize inexpensive, prepackaged aromatherapy compositions for selective diffusion into the passenger compartment of the vehicle.

Other objectives and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1-9. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

A method 900 for selectively inducing various emotional states in a vehicle with multiple aromatherapy compositions is referenced in FIGS. 1-9. In one embodiment, method 900 strategically infuses multiple, eclectic aromatherapy compositions into an interior passenger compartment of a vehicle to create a desired emotional state for a passenger in the passenger compartment. The passenger selects an appropriate aromatherapy composition, or mixtures thereof, to achieve a desired emotional state. The passenger may change aromatherapy compositions at regular durations to achieve multiple emotional states while in the same duration in the passenger compartment. The passenger may also mix multiple aromatherapy compositions to create a user defined emotional state.

Those skilled in the art will recognize that aromatherapy is the practice of using the natural oils extracted from flowers, bark, stems, leaves, roots or other parts of a plant to enhance psychological and physical well-being. The inhaled aroma from these essential oils is widely believed to stimulate brain function; and thereby the emotional state. The present invention provides eclectic aromatherapy compositions that can be used alone, changed after a duration, or mixed to produce a desired emotional state.

The aromatherapy compositions for the present disclosure may include, without limitation, a lavender and potpourri aromatherapy formula, a sweet apple aromatherapy formula, a rose and potpourri aromatherapy formula, a relaxing aromatherapy formula, an anxiety relief aromatherapy formula, an energy inducing aromatherapy formula, a happiness inducing aromatherapy formula, and an anger reducing aromatherapy formula.

According to one aspect of the present invention, a method for selectively inducing various emotional states of occupants in a vehicle with multiple aromatherapy compositions, the method comprising, formulating multiple aromatherapy compositions, whereby each aromatherapy composition is configured to induce a unique emotional state; integrating at least one of the multiple aromatherapy compositions into a ventilation system of a vehicle; vaporizing the at least one of the multiple aromatherapy compositions; diffusing the at least one of the multiple aromatherapy compositions into a passenger compartment of the vehicle; inducing an emotional state in a driver or passenger; selecting a subsequent aromatherapy composition; integrating the subsequent aromatherapy composition into the ventilation system of the vehicle to induce a subsequent emotional state in the passenger; mixing multiple aromatherapy compositions; and integrating the mixed aromatherapy compositions into the ventilation system of the vehicle to induce a user defined emotional state in the driver or passenger.

According to another aspect of the present invention, a kit comprising multiple aromatherapy compositions for selectively inducing various emotional states in a closed compartment, wherein the kit comprises multiple aromatherapy compositions including a lavender and potpourri aromatherapy composition; a sweet apple aromatherapy composition; a rose and potpourri aromatherapy composition; a relaxing aromatherapy composition; an anxiety relief aromatherapy composition; an energy inducing aromatherapy composition; a happiness inducing aromatherapy composition; and an anger reducing aromatherapy composition, wherein the kit allows integrating at least one of the multiple aromatherapy compositions into a ventilation system of the closed compartment, thereby allowing vaporization and diffusion of the at least one of the multiple aromatherapy compositions into the compartment.

According to another aspect of the present invention, the method further includes a step of flushing the ventilation system of the vehicle.

According to another aspect of the present invention, the method further includes a step of automating the integration of the multiple aromatherapy compositions into the ventilation systems.

According to another aspect of the present invention, the aromatherapy compositions are available in gel or solid state or in powdered form in addition to a liquid state, thereby allowing direct placement of the aromatherapy compositions into the exhaust pathway of the vehicle ventilation system.

Figure 1:
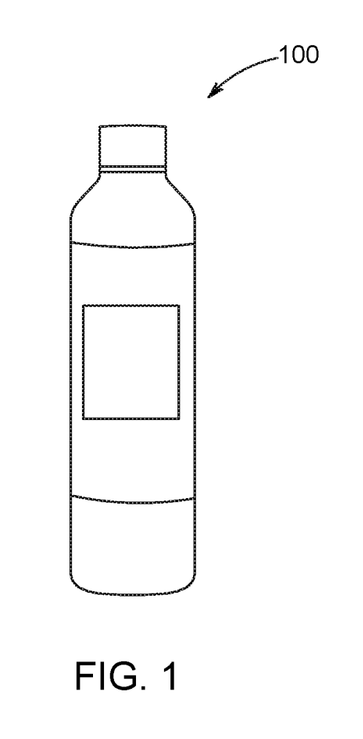
FIG. 1 illustrates an exemplary aromatherapy formulation of the lavender and potpourri aromatherapy formula stored in a closed container, in accordance with an embodiment of the present invention.

FIG. 1 illustrates an exemplary formulation of the lavender and potpourri aromatherapy formula 100, whereby lavender concentrate is mixed with liquid potpourri/simmer oil to form a 340 milligram concentrate. Though other formulations for lavender and potpourri that are known in the art may be used.

Figure 2:
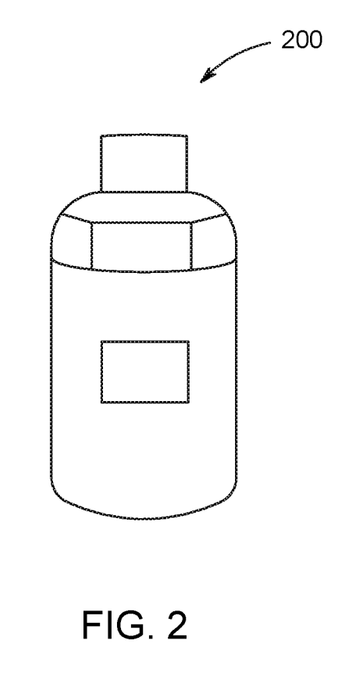
FIG. 2 illustrates an exemplary formulation of the sweet apple aromatherapy formula stored in a closed container, in accordance with an embodiment of the present invention.

FIG. 2 illustrates an exemplary formulation of the sweet apple aromatherapy formula 200, whereby Gonesh® Reed Diffuser Oil Refill of sweet apple is used. Though other formulations for sweet apple that are known in the art may be used.

Figure 3:
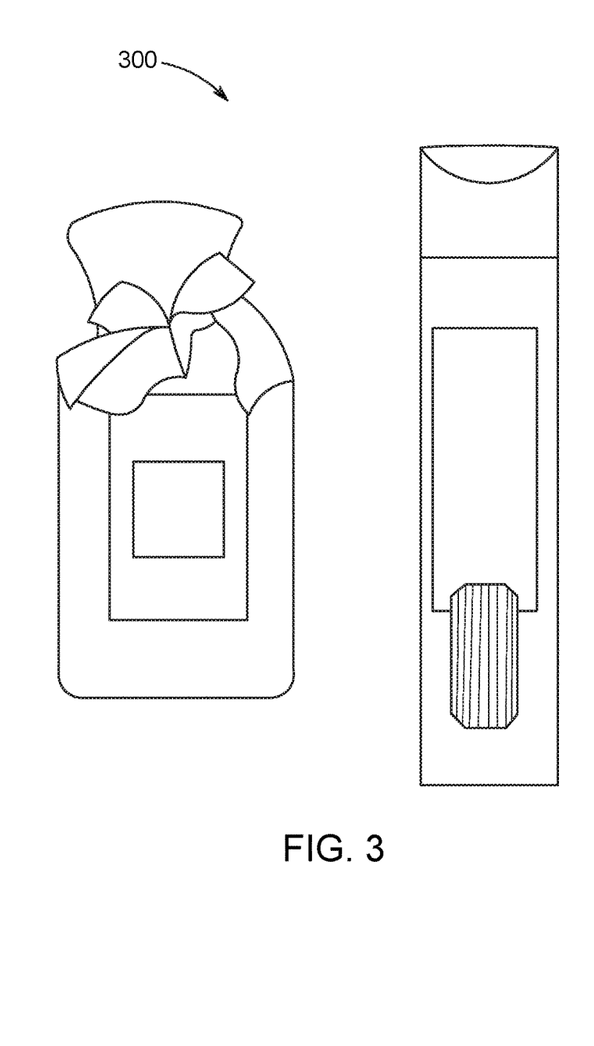
FIG. 3 illustrates an exemplary formulation of the rose and potpourri aromatherapy formula in a powdered form and as incense stick, in accordance with an embodiment of the present invention.

FIG. 3 illustrates an exemplary formulation of the rose and potpourri aromatherapy formula 300, whereby lavender concentrate is mixed with 175 quarts of dry rose potpourri to form a 328 milligram concentrate. FIG. 3 shows the exemplary formulations available in different forms such as powder or as incense sticks. Though other formulations for rose and potpourri that are known in the art may also be used.

Figure 4:
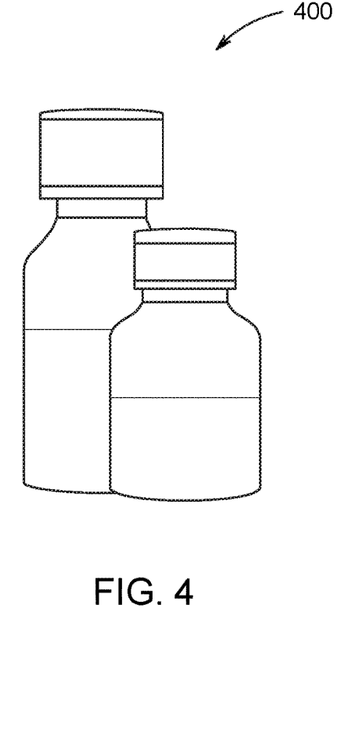
FIG. 4 illustrates an exemplary relaxing aromatherapy formula in liquid form stored in a closed container, in accordance with an embodiment of the present invention.

FIG. 4 illustrates an exemplary relaxing aromatherapy formula 400, whereby 1 ounce of carrier oil is mixed with 7 drops of Roman Chamomile and 5 drops of Lavender. Though other formulations for relaxation that are known in the art may be used.

Figure 5:
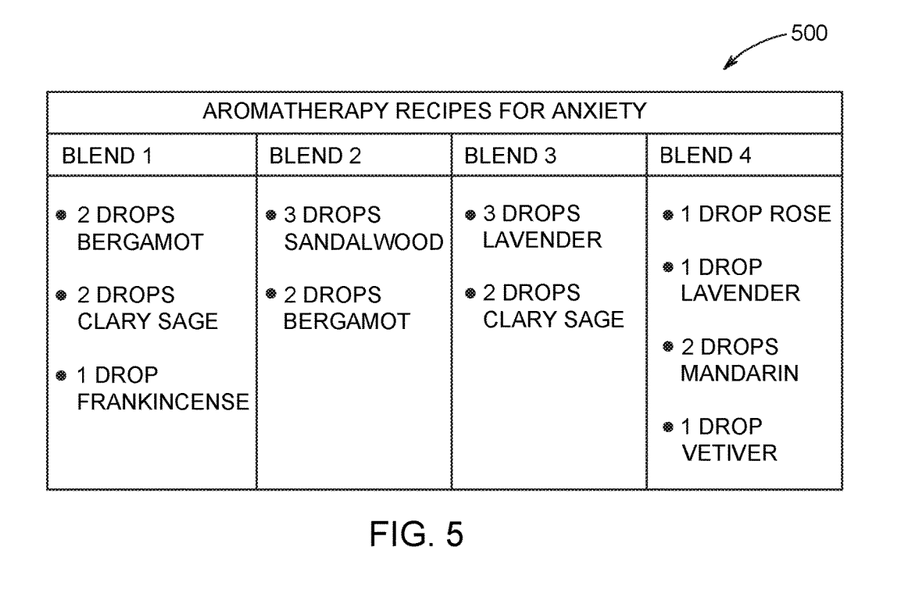
FIG. 5 illustrates a table showing an exemplary anxiety relief aromatherapy formula in plurality of blends, in accordance with an embodiment of the present invention.

FIG. 5 illustrates an exemplary anxiety relief aromatherapy formula 500 in several blends represented in a tabular form, whereby blend 1 is a mixture of 2 drops Bergamot oil mixed with 2 drops of Clary Sage oil and 2 drops of Frankincense oil. Though other formulations for anxiety relief that are known in the art may be used.

According to another aspect of the present invention, another blend (blend 2) of the anxiety relief aromatherapy comprises 3 drops of Sandalwood oil and 2 drops of Bergamot oil.

According to another aspect of the present invention, another blend (blend 3) of anxiety relief aromatherapy composition comprises 3 drops of Lavender oil and 2 drops of Clary Sage oil.

According to another aspect of the present invention, another blend (blend 4) of anxiety relief aromatherapy composition comprises 1 drop of Rose oil, 1 drop of Lavender oil, 2 drops of Mandarin oil and 1 drop of Vetiver oil.

Figure 6:
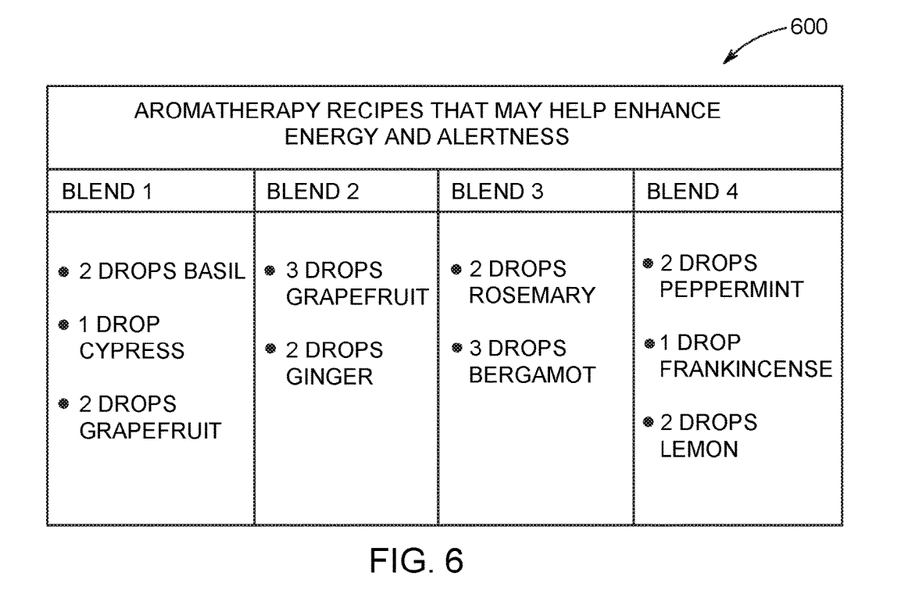
FIG. 6 illustrates a table showing an exemplary energy inducing aromatherapy formula in plurality of blends, in accordance with an embodiment of the present invention.

FIG. 6 illustrates an exemplary energy inducing aromatherapy formula 600 in several blends represented in a tabular form, whereby blend 1 comprises a mixture of 2 drops of Basil mixed with 1 drop of Cypress and 2 drops of Grapefruit. Though other formulations for energy inducement that are known in the art may be used.

According to another aspect of the present invention, another blend (blend 2) of the energy inducing aromatherapy composition comprises 3 drops of Grapefruit oil and 2 drops of Ginger oil.

According to another aspect of the present invention, another blend (blend 3) of the energy inducing aromatherapy composition comprises 2 drops of Rosemary oil and 3 drops of Bergamot oil.

According to another aspect of the present invention, another blend (blend 4) of the energy inducing aromatherapy composition comprises 2 drops of Peppermint oil, 1 drop of Frankincense oil and 2 drops of Lemon oil.

Figure 7:
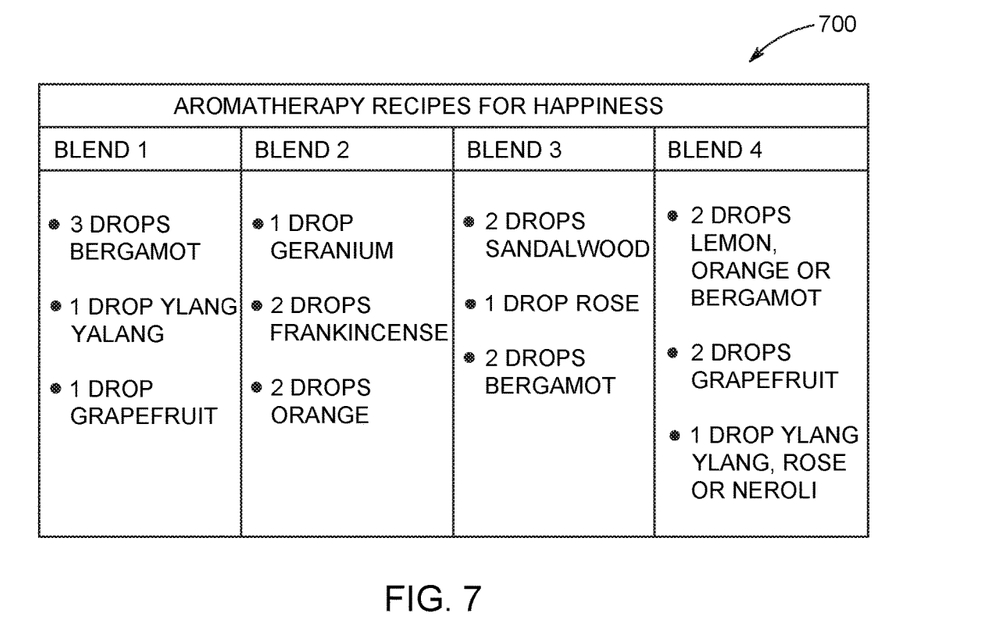
FIG. 7 illustrates a table showing an exemplary happiness inducing aromatherapy formula in plurality of blends, in accordance with an embodiment of the present invention.

FIG. 7 illustrates an exemplary happiness inducing aromatherapy formula 700 in several blends represented in a tabular form, whereby blend 1 comprises a mixture of 3 drops of Bergamot mixed with 1 drop of Ylang Ylang and 1 drop of Grapefruit. Though other formulations for happiness inducement that are known in the art may be used.

According to another aspect of the present invention, another blend (blend 2) of the happiness inducing aromatherapy composition comprises 1 drop of Geranium oil, 2 drops of Frankincense oil and 2 drops of Orange oil.

According to another aspect of the present invention, another blend (blend 3) of the happiness inducing aromatherapy composition comprises 2 drops of Sandalwood oil, 1 drop of Rose oil and 2 drops of Bergamot oil.

According to another aspect of the present invention, another blend (blend 4) of the happiness inducing aromatherapy composition comprises 2 drops of Lemon, Orange or Bergamot oil, 2 drops of Grapefruit oil and 1 drop of Ylang Ylang, Rose or Neroli oil.

Figure 8:
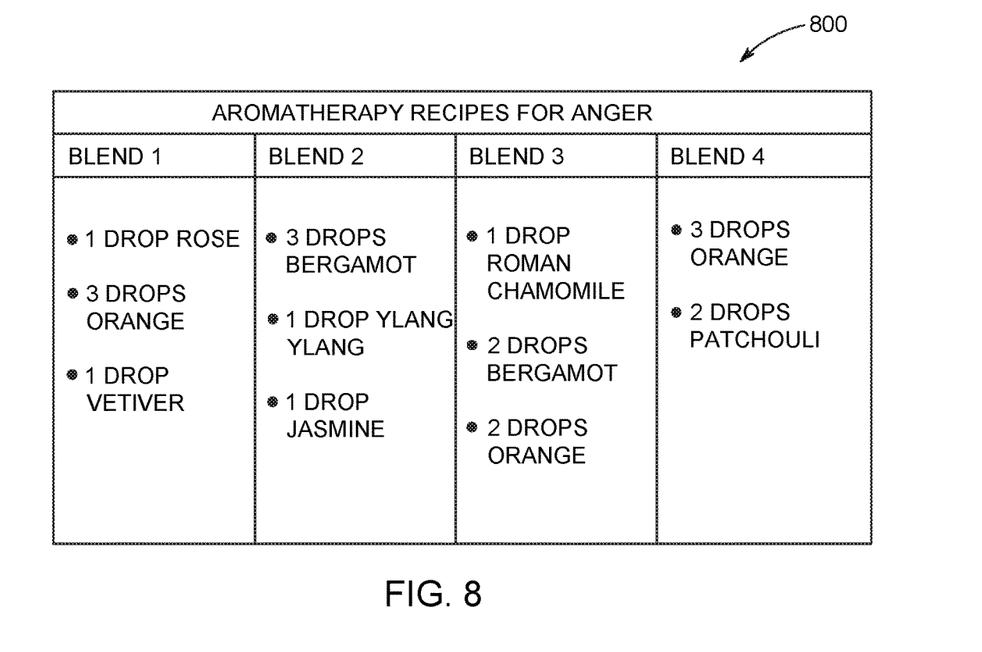
FIG. 8 illustrates a table showing an exemplary anger reducing aromatherapy formula in plurality of blends, in accordance with an embodiment of the present invention.

FIG. 8 illustrates an exemplary anger reducing aromatherapy formula 800 in several blends represented in a tabular form, whereby blend 1 comprises a mixture of 1 drop of Rose mixed with 3 drops of Orange and 1 drop of Vetiver. Though other formulations for anger reduction that are known in the art may be used.

According to another aspect of the present invention, another blend (blend 2) of the anger reducing aromatherapy composition comprises 3 drops of Bergamot oil, 1 drop of Ylang Ylang oil and 1 drop of Jasmine oil.

According to another aspect of the present invention, another blend (blend 3) of the anger reducing aromatherapy composition comprises 1 drop of Roman Chamomile oil, 2 drops of Bergamot oil and 2 drops of Orange oil.

According to another aspect of the present invention, another blend (blend 4) of the anger reducing aromatherapy composition comprises 3 drops Orange oil and 2 drops of Patchouli oil.

The induced emotional states from these various aromatherapy compositions may include, without limitation, happiness, nostalgia, inspirational, energy, an emotional state that provides relief from anxiety, an emotional state that provides management of anger, an emotional state that provides relaxation, and an emotional state that provides relief from stress. Mixture of the compositions may, however, create different emotional states.

In any case, the passenger chooses the aromatherapy compositions and easily integrates them into the vehicle for diffusion into the passenger compartment. This allows the passenger to select a desired aromatherapy composition based on a desired emotional state—at least while in the passenger compartment of the vehicle.

At least one of the multiple aromatherapy compositions is integrated into the ventilation system of the vehicle for diffusion into the passenger compartment. In one embodiment, the aromatherapy composition is added to a reservoir containing wiper fluid. For example, pouring about 1 to 1.5 ounces of the at least one of the multiple aromatherapy compositions into a gallon of wiper fluid in a wiper fluid reservoir. Those skilled in the art will recognize that when the vehicle's air conditioning, heating, cooling, or ventilating system is running, the aromatherapy composition and wiper fluid can be released into the ventilation system and vaporized for diffusion into the passenger compartment.

In an exemplary embodiment of the present invention, commonly used car windshield care products such as Rain-X can be combined with popular scent like Gain laundry detergent or Gain scent to form a mood-elevating aroma therapy composition that can be combined with windshield washer fluid where it may be dispensed or applied on the exterior of the windshield. Further other combination of scents with windshield care compositions that are known in the art can be mixed to form an aroma therapy composition that can be added to windshield washer fluid without departing from the scope and the spirit of the present invention.

In another embodiment, the aromatherapy composition may, however, be sprayed directly onto the windshield of the vehicle while the vehicle's air conditioning, heating, cooling, or ventilating system is running. Though in other embodiments, the aromatherapy compositions may be in a gel or solid state that allows for direct placement into the exhaust pathway of the vehicle ventilation system.

Any of these integration means causes the aromatherapy composition to vaporize and be drawn into the vehicle passenger compartment where it diffuses into the ambient air of the passenger compartment. Thus, a vaporized diffusion of aromatherapy is diffused into the passenger compartment of the vehicle, causing inducement of an emotional state based on the selected aromatherapy composition, or combinations thereof.

Figure 9:
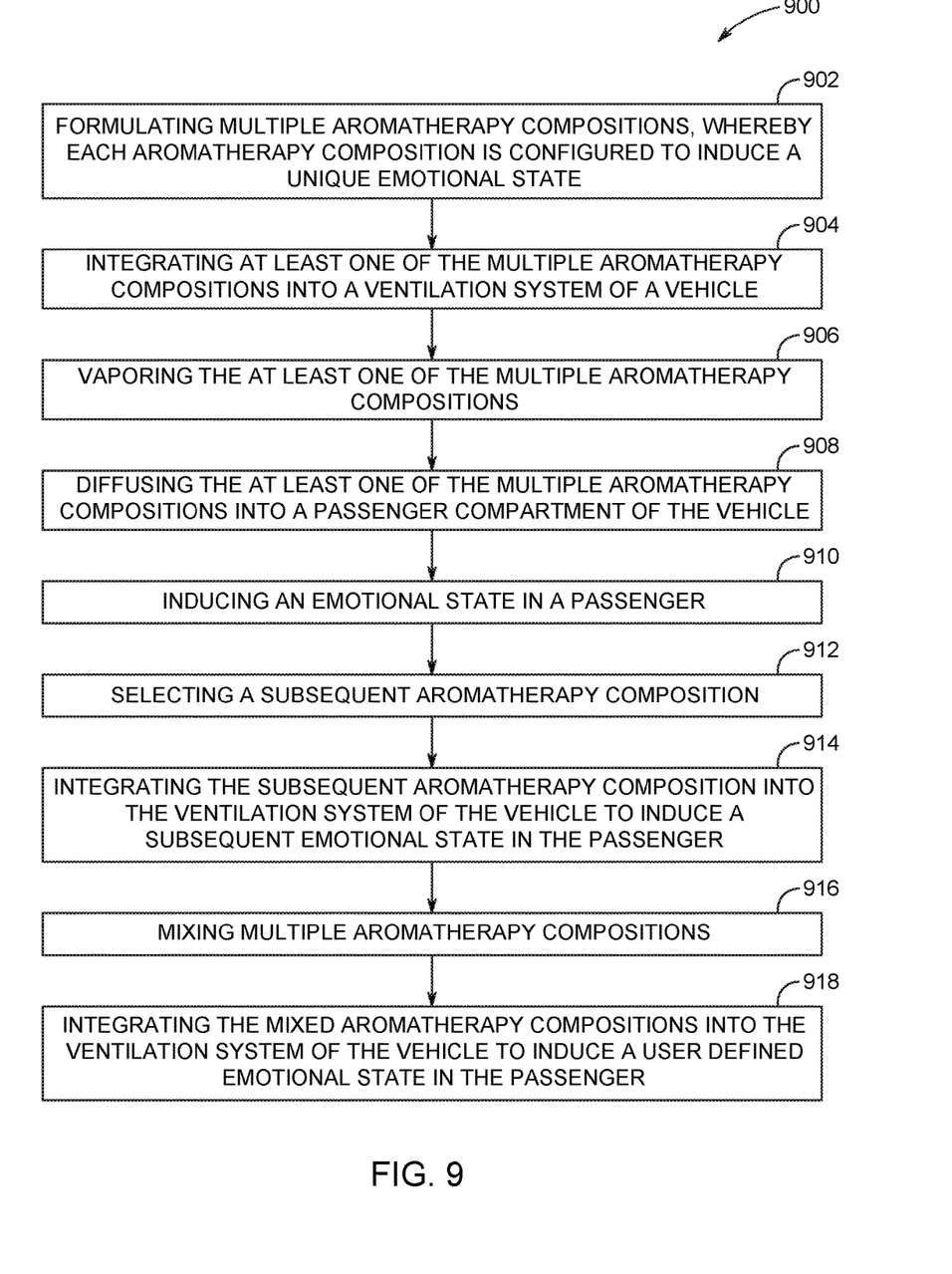
FIG. 9 illustrates a flowchart of an exemplary method for selectively inducing various emotional states in a vehicle with multiple aromatherapy compositions, in accordance with an embodiment of the present invention.

Once diffused in the passenger compartment, the emotional state correlating to the selected aromatherapy composition is induced. The method 900, however, allows the passenger to change the emotional state throughout the duration of time in the passenger compartment. For example, on a long trip, the passenger may change the aromatherapy compositions multiple times to achieve different emotional states. This is possible because of the ease of replacing or mixing the aromatherapy composition into the ventilation system of the vehicle.

In some embodiments, the passenger may: 1) use the same aromatherapy composition throughout the duration in the passenger compartment to maintain the same emotional state; 2) change the aromatherapy composition at any time during the duration in the passenger compartment to change the emotional state; or 3) mix multiple aromatherapy compositions to create a passenger-defined emotional state. These options enable great flexibility for selectively altering emotional states while on a long trip, or during extended durations in a passenger compartment.

FIG. 9 illustrates a flowchart for an exemplary method 900 for selectively inducing various emotional states in a vehicle with multiple aromatherapy compositions. The method 900 comprises an initial Step 902 of formulating multiple aromatherapy compositions, whereby each aromatherapy composition is configured to induce a unique emotional state.

In one embodiment, a Step 904 comprises integrating at least one of the multiple aromatherapy compositions into a ventilation system of a vehicle. The step of integrating at least one of the multiple aromatherapy compositions into a ventilation system of a vehicle may further comprise mixing about 1 to 1.5 ounces of the aromatherapy composition with a gallon of wiper fluid and pouring the mixture into a wiper fluid reservoir.

In some embodiments, the method 900 may include an additional Step 906 of vaporing the at least one of the multiple aromatherapy compositions. A Step 908 comprises diffusing the at least one of the multiple aromatherapy compositions into a passenger compartment of the vehicle. A Step 910 further comprises inducing an emotional state in a passenger. A Step 912 may include selecting a subsequent aromatherapy composition. A Step 914 includes integrating the subsequent aromatherapy composition into the ventilation system of the vehicle to induce a subsequent emotional state in the passenger.

The method 900 may include a further Step 916 of mixing multiple aromatherapy compositions. A Step 918 comprises integrating the mixed aromatherapy compositions into the ventilation system of the vehicle to induce a user defined emotional state in the passenger. Alternative steps to the method 900 may include flushing the ventilation system of the vehicle; and a step of automating the integration of the multiple aromatherapy compositions into the ventilation systems.

According to another embodiment of the present invention, a kit comprising multiple aromatherapy compositions for selectively inducing various emotional states in a closed compartment, wherein the kit comprises multiple aromatherapy compositions including a lavender and potpourri aromatherapy composition; a sweet apple aromatherapy composition; a rose and potpourri aromatherapy composition; a relaxing aromatherapy composition; an anxiety relief aromatherapy composition; an energy inducing aromatherapy composition; a happiness inducing aromatherapy composition; and an anger reducing aromatherapy composition, wherein the kit allows integrating at least one of the multiple aromatherapy compositions into a ventilation system of the closed compartment, thereby allowing vaporization and diffusion of the at least one of the multiple aromatherapy compositions into the compartment. One objective of the present invention is to induce an emotional state of an occupant in a passenger compartment of a vehicle.

Another objective is to enable the passenger to change or mix the aromatherapy compositions, so as to induce a subsequent or user defined emotional state.

Yet another objective is to enable facilitated integration of the aromatherapy compositions into a ventilation system of the vehicle.

Yet another objective is to utilize inexpensive, prepackaged aromatherapy compositions for selective diffusion into the passenger compartment of the vehicle.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method for user selectively inducing various emotional states of occupants in a vehicle with multiple aromatherapy compositions, the method comprising:
    formulating multiple aromatherapy compositions, whereby each aromatherapy composition is configured to induce a unique emotional state;
    integrating at least one of the multiple aromatherapy compositions into a ventilation system of a vehicle;
    vaporing the at least one of the multiple aromatherapy compositions;
    diffusing the at least one of the multiple aromatherapy compositions into a passenger compartment of the vehicle;
    inducing an emotional state in an occupant;
    selecting a subsequent aromatherapy composition;
    integrating the subsequent aromatherapy composition into the ventilation system of the vehicle to induce a subsequent emotional state in the occupant;
    mixing multiple aromatherapy compositions; and
    integrating the mixed aromatherapy compositions into the ventilation system of the vehicle to induce a user defined emotional state in the occupant which composition is selected by the occupant.

2. The method of claim 1, wherein the multiple aromatherapy compositions include at least one of the following: a lavender and potpourri aromatherapy formula, a sweet apple aromatherapy formula, a rose and potpourri aromatherapy formula, a relaxing aromatherapy formula, an anxiety relief aromatherapy formula, an energy inducing aromatherapy formula, a happiness inducing aromatherapy formula, and an anger reducing aromatherapy formula.

3. The method of claim 1, wherein the induced emotional state includes at least one of the following: happiness, nostalgia, inspirational, energy, an emotional state that provides relief from anxiety, an emotional state that provides management of anger, an emotional state that provides relaxation, and an emotional state that provides relief from stress.

4. The method of claim 1, wherein the step of integrating at least one of the multiple aromatherapy compositions into a ventilation system of a vehicle, comprises mixing about 1 to 1.5 ounces of the aromatherapy composition with a gallon of windshield washer fluid and pouring the mixture into a wiper fluid reservoir.

5. The method of claim 1, further including a step of flushing the ventilation system of the vehicle.

6. The method of claim 1, further including a step of automating the integration of the multiple aromatherapy compositions into the ventilation systems.

7. The method of claim 1, wherein the aromatherapy compositions is available in gel or solid state in addition to a liquid state, thereby allowing direct placement of the aromatherapy compositions into the exhaust pathway of the vehicle ventilation system.

8. The method of claim 1, wherein the aromatherapy compositions further comprises a combination of mood-elevating scents with windshield care compositions that can be mixed with windshield washer fluid.

9. The method of claim 1, wherein the occupant may change aromatherapy compositions at regular durations to achieve multiple emotional states while in a same duration in the vehicle.

* * * * *